United States Patent [19]

Missanelli et al.

[11] Patent Number: 5,193,542
[45] Date of Patent: Mar. 16, 1993

[54] PERIPARTUM OXIMETRIC MONITORING APPARATUS

[76] Inventors: John S. Missanelli; Mearl Naponic, both of 8851 Center Dr., Ste. 301, La Mesa, Calif. 92042

[21] Appl. No.: 856,999

[22] Filed: Mar. 25, 1992

Related U.S. Application Data

[63] Continuation of Ser. No. 646,422, Jan. 28, 1991, abandoned.

[51] Int. Cl.$^5$ .................................................. A61B 5/00
[52] U.S. Cl. ..................................... 128/633; 356/41; 128/666
[58] Field of Search .............................. 128/633-634, 128/665-666; 356/41

[56] References Cited

U.S. PATENT DOCUMENTS

| 3,810,460 | 5/1974 | Van Nie | 128/664 |
| 4,334,544 | 6/1982 | Hill et al. | 128/666 |
| 4,685,464 | 8/1987 | Goldberger et al. | 128/633 |

FOREIGN PATENT DOCUMENTS 2635221 9/1978 Fed. Rep. of Germany ...... 128/666

Primary Examiner—Lee S. Cohen
Assistant Examiner—Robert L. Nasser, Jr.

[57] ABSTRACT

An oximeter probe is introduced through the vaginal canal and applied to the scalp or other readily accessible part of the fetus while still in utero. The fetal oxygenation is monitored during the entire labor and delivery period to obtain instantaneous indications of any peripartum fetal distress. The probe comprises a clamping device which can be easily manipulated within the narrow confines of the partially dilated cervix.

2 Claims, 1 Drawing Sheet

U.S. Patent      Mar. 16, 1993      5,193,542
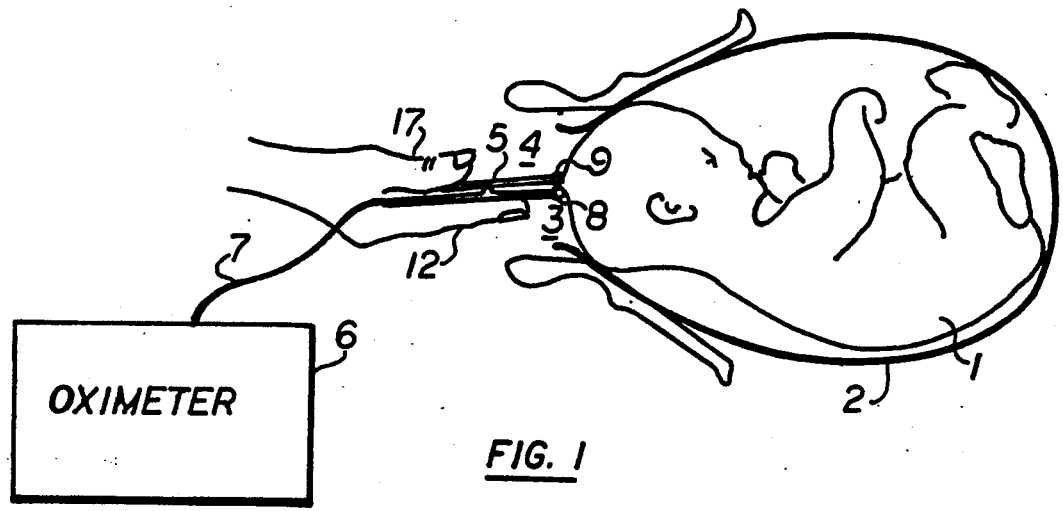
FIG. 1
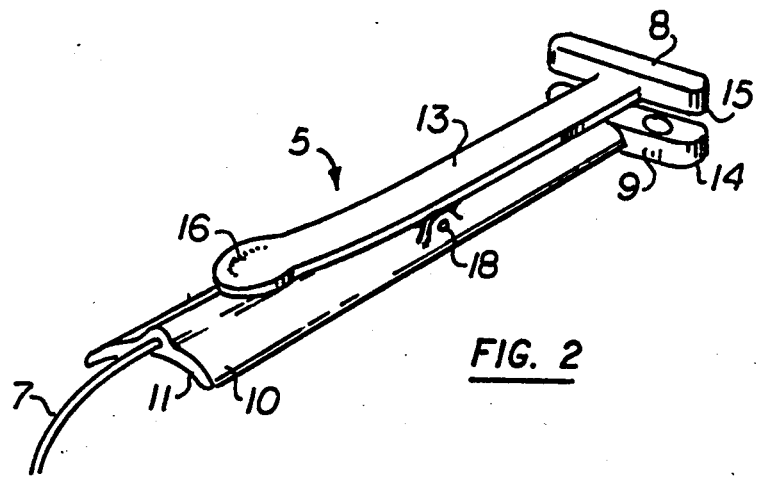
FIG. 2
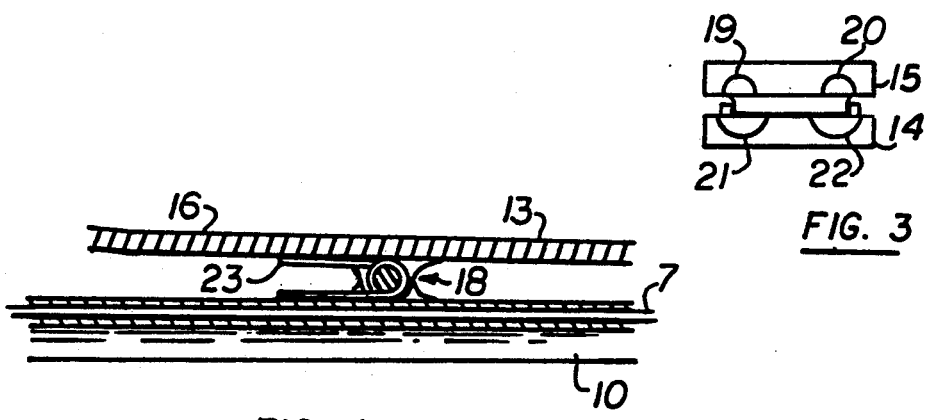
FIG. 3
FIG. 4

PERIPARTUM OXIMETRIC MONITORING APPARATUS

This is a continuation of Ser. No. 07/646422, filed Jan. 28, 1991, now abandoned.

FIELD OF THE INVENTION

This invention relates to apparatuses for monitoring the vital functions of a patient and to methods for using said apparatuses during surgical interventions.

BACKGROUND OF THE INVENTION

Peripartum is a traumatic and hazardous process for both the mother and the child during which any complication may result in the death of the fetus or some disastrous impairment such as cerebral palsy or permanent kinetic disability. Currently the only scientific monitoring has been limited to the measurement of uterine contractions and fetal heart rate. Other sophisticated instruments are now available for monitoring the vital signs of a patient which should, but have not yet been applied to fetal life for lack of appropriate and practical method and instrumentation. One of the most revealing instruments used in monitoring patients during surgical interventions is the pulse oximeter which can accurately measure arterial hemoglobin oxygen saturation by means of a non-invasive probe. The monitoring of blood oxygenation during peripartum progress would give an early warning of fetal distress requiring obstetrical intervention and would eliminate the subjective determination of fetal well-being based only on measurements of uterine contractions and fetal heartbeat only.

SUMMARY OF THE INVENTION

The principal object of the invention is to provide a continuous monitoring of the fetal blood oxygenation during peripartum in order to obtain early warning of any fetal distress. This and other useful objects are achieved by attaching a oximeter probe to a tissue section of the fetus while it is still in utero during the early manifestations of labor.

BRIEF DESCRIPTION OF THE DRAWINGS

FIG. 1 is a diagram illustrating the attachment of the oximeter probe to the fetal scalp of the fetus;

FIG. 2 is a perspective view of the oximeter probe;

FIG. 3 is a cross-sectional diagrammatic view of the distal end of the probe; and FIG. 4 is a cross-sectional view of the median section of the probe.

DESCRIPTION OF THE PREFERRED EMBODIMENT OF THE INVENTION

Referring now to the drawing, there is shown diagrammatically in FIG. 1 a fetus 1 still in utero and surrounded by the amniotic membrane 2. At the onset of labor the attending physician makes a vaginal examination to determine the position of the fetus after having broken the amniotic membrane 2 at the opening 3 of the vaginal canal 4. The physician by tactile contact determines the most accessible part of the fetus such as the scalp or one ear in case of brow presentation, the nose in case of face presentation, or an arm or a leg in case of a breach or shoulder presentation. The physician then inserts through the vaginal canal 4 a probe 5 attachable to a pulse oximeter 6 by a flexible cable 7, and clips the distal end 8 of the probe to the accessible part of the fetus such as the scalp 9. The probe 5 will remain attached to the fetus during the entire peripartum process allowing the physician to monitor the blood oxygenation of the fetus during the entire delivery procedure.

The probe 5 whose configuration is illustrated in FIGS. 2 and 3, comprises a first elongated handle 10 having an arcuate undersurface 11 designed to rest against the inner surface of the attending physician's index 12. A second member 13 is rockingly mounted above the first member 10 to form a clamping device with two reciprocating jaws 14, 15 attached to the distal ends of the first and second members respectively. A lever 16 extending toward the proximal end of the probe can be manipulated by the thumb 17 of the attending physician to open and close the distal jaws 14, 15. A spring, 23 shown in FIG. 4 of the drawing, is integrated within the hinged fulcrum mechanism 18 of the probe, and is biased to force the two jaws 14, 15 together. It can now be understood that the distal end 8 of the probe can thus be clamped on a portion of fetal tissue to sense the oxygenation of the blood circulating through it.

As more specifically illustrated in FIG. 3, the upper jaw 15 houses a pair of light emitting diodes 19, 20. The lower jaw 14 houses a pair of light detectors 21, 22 which are in line with the light emitting diodes 19, 20. According to known principles of pulse oximetry, the light emitting diodes emits lights of different wave lengths. The light detectors 21, 22 measure the amount of light which is not absorbed by the blood circulation through the interposed section of tissue. The difference between the two light measurements is used by the oximeter to determine the arterial hemoglobin oxygen saturation.

While the preferred embodiments of the invention have been described, modifications can be made and other embodiments may be devised without departing from the spirit of the invention and the scope of the appended claims.

What is claimed is:

1. In combination with a blood oxygenation measurement apparatus, a vaginal probe for attachment to a fetus in utero, said probe comprising:

a pair of resiliently openable, interfacing jaws, a first of said jaws having at least one light emitter and a second of said jaws having at least one light detector in line with said light emitter, an elongated handle having an undersurface arcuate to an axis substantially parallel to and spaced apart from the largest dimension of said handle sized and shaped to rest against the surface of an attending person's finger, said handle extending from one of said jaws, an elongated lever extending from the other of said jaws parallely to said handle and having a fulcrum point on an upper surface portion of said handle; and a resilient means for baising the jaws towards each other.

2. The combination of claim 1, wherein said fulcrum point comprises:

a hinged mechanism; and said resilient means comprises a coil spring integrated within said hinged mechanism.

* * * * *